Ts011684499B2

(12) United States Patent
Zheng et al.

(10) Patent No.: US 11,684,499 B2
(45) Date of Patent: Jun. 27, 2023

(54) STENT DELIVERY SYSTEM (71) Applicant: Shanghai Elitek Biosciences Co., Ltd, Shanghai (CN)

(72) Inventors: Zhongwei Zheng, Shanghai (CN); Hang Yan, Shanghai (CN)

(73) Assignee: Shanghai Elitek Biosciences Co., Ltd., Shanghai (CN)

( * ) Notice: Subject to any disclaimer, the term of this patent is extended or adjusted under 35 U.S.C. 154(b) by 0 days.

(21) Appl. No.: 16/980,565

(22) PCT Filed: Sep. 9, 2018

(86) PCT No.: PCT/CN2018/104737
§ 371 (c)(1),
(2) Date: Oct. 2, 2020

(87) PCT Pub. No.: WO2020/047876
PCT Pub. Date: Mar. 12, 2020

(65) Prior Publication Data
US 2021/0186727 A1 Jun. 24, 2021

(51) Int. Cl.
*A61F 2/95* (2013.01)
*A61F 2/966* (2013.01)

(52) U.S. Cl.
CPC ............ *A61F 2/9517* (2020.05); *A61F 2/966* (2013.01); *A61F 2002/9665* (2013.01)

(58) Field of Classification Search
CPC .................... A61F 2/9517; A61F 2/966; A61F 2002/9665; A61F 2250/0039
See application file for complete search history.

(56) References Cited

U.S. PATENT DOCUMENTS 6,322,586 B1* 11/2001 Monroe .............. A61M 25/001
606/108
2006/0229697 A1* 10/2006 Gerdts .................... A61F 2/966
623/1.11
(Continued)

FOREIGN PATENT DOCUMENTS

CN 200520070630 U 6/2006
CN 102028570 A 4/2011
(Continued)

OTHER PUBLICATIONS

International Search Report in PCT Application PCT/CN2018/104737, dated May 31, 2019, 3 pages.

*Primary Examiner* — Timothy J Neal
*Assistant Examiner* — Andrew P. Restaino
(74) *Attorney, Agent, or Firm* — Zhu Lehnhoff LLP (57) ABSTRACT

A stent delivery system is described. The system includes an outer sleeve assembly with an outer sleeve body, an outer sleeve handle fixed to one end of the outer sleeve body, and an outer sleeve tip connected to an opposing end of the outer sleeve body. The system also includes an inner sleeve assembly, which has a push tube sleeved in the outer sleeve body, an inner sleeve handle fixed to the rear end of the push tube, a stent placing tube connected to the front end of the push tube, and an inner sleeve tip set at the front end of the stent placing tube. The system also includes a snap ring fixed on an outer wall of the push tube and provided between the outer sleeve handle and the inner sleeve handle. The outer sleeve tip includes a stepped surface.

6 Claims, 3 Drawing Sheets (56) References Cited

U.S. PATENT DOCUMENTS

| | | | |
|---|---|---|---|
| 2006/0259120 A1 | 11/2006 | Adel et al. | |
| 2008/0234796 A1 | 9/2008 | Jurgen | |
| 2010/0298931 A1* | 11/2010 | Quadri | A61F 2/95 623/2.11 |
| 2014/0107757 A1* | 4/2014 | Dorn | A61F 2/966 623/1.11 |
| 2014/0257456 A1* | 9/2014 | Cannon | A61F 2/966 623/1.11 |
| 2018/0116844 A1* | 5/2018 | Keller | A61F 2/2436 |

FOREIGN PATENT DOCUMENTS

| | | |
|---|---|---|
| CN | 102038565 A | 5/2011 |
| CN | 201120539751.2 U | 9/2012 |
| CN | 201310010362 A | 5/2013 |
| CN | 204709092 U | 10/2015 |
| CN | 206612865 U | 11/2017 |

* cited by examiner

STENT DELIVERY SYSTEM

PRIORITY CLAIM

The present application is a U.S. Nationalization of PCT Application PCT/CN2018/104737, filed on Sep. 9, 2018, presently pending, the contents of which are incorporated-by-reference.

FIELD OF THE INVENTION

The present invention relates to the field of medical devices and particularly relates to a stent delivery system.

BACKGROUND OF THE INVENTION

At present, commercial or general esophageal stent release pushers are generally a combination of components such as adjusting handles, fixed handles, handles, outer tubes, inner tubes, thin tubes, stent cavities, compression stents, and guide heads. There is a certain gap between the outer tube and the inner tube of the pusher to ensure that they can slide relative to each other. The stent is placed in the cavity formed by the outer tube and the thin tube (called the stent cavity), and the length of the stent cavity can be adjusted to meet the needs of different lengths of the stent through the mutual movement of the inner tube and the thin tube. When the outer tube is withdrawn, the compression stent between the thin tube and the outer tube is gradually released and opened.

For example, the Chinese patent document with application number CN200520070630.2 discloses a coating film stent conveyor, which is mainly composed of an outer sleeve and an inner core. The outer sleeve is coated sheathed outside the inner core, and the inner core is composed of a guide head, a shaft core tube, and a conveying rod. The front end of the shaft core tube is connected to the guide head, and the rear end of the shaft core tube is connected to the conveying rod. The stent placing segment is arranged at the rear of the guide head of the shaft core tube, the length of which is larger than the diameter of the esophageal stent and slightly smaller than the shaft core tube. A stent is placed on the shaft core tube, and the outer sleeve presses the stent on the shaft core tube. The outer sleeve is slowly withdrawn when the conveyor is positioned in the narrow section of lumens, and the stent is deployed and detached from the shaft core tube, then the guide head is retracted to the outer sleeve and exits the lumen with the same. The coating film stent conveyor of this utility model can conveniently enter the lumen, reduce the difficulty of stent release, improve the accuracy of stent delivery, help patients to prolong survival and improve quality of life.

As another example, the Chinese patent document with application number CN 201310010362.4 discloses an esophageal stent conveyor, including an outer sheath tube, a core tube, a push tube, a guide head, a developing identification ring, a radiopaque marking ring, a front handle, a rear handle and a security lock sleeve, wherein a compression sleeve and a tension sleeve are provided, a positioning hole and a recovery hole are sequentially arranged between the perforation of the outer sheath tube at the center of the front handle and the locking screw hole, the rear end portion of the inner wall of the positioning hole is provided with clamping grooves along the axis circumferential array, the compression sleeve is formed by a annular top table, a tensioning large cylindrical sleeve body and a positioning small cylindrical sleeve body fixedly connected along the same axis, the outer end of the inner hole of the annular top table is provided with a tapered positioning hole, the tension sleeve is composed of a cylindrical fixed sleeve body and a tapered table body at the front end of the cylindrical fixed sleeve body, the tension sleeve is provided with tension through grooves along an axial circumferential array and along one end of the tapered table body, the compression sleeve and the tension sleeve are respectively sleeved on the push tube, one end of the tension sleeve is connected with the security lock sleeve through the fixed sleeve body and the other end corresponds to the compression sleeve, and the compression sleeve is sleeved on the rear end of the outer sheath tube and fixed on the front handle. It has the advantages of novel structure, fast operation, accurate judgment, low withdrawal resistance, short operation time, and small patient pain, etc.

As another example, the Chinese patent document with application number CN 201120539751.2 discloses a controllable esophageal stent release pusher, including an esophageal stent release pusher, which includes an adjusting handle, a fixed handle, a handle, an external tube, an inner tube, a thin tube, a guide head, a stent cavity, a stent, wherein the outer tube is provided with a scale line, the stent cavity is composed of the distal end of the inner tube, the proximal end of guide head and the outer tube, the stent cavity is provided with a stent, a thin tube is arranged at the proximal end of the stent cavity, the thin tube is in communication with the guide head, the thin tube is provided with a hole, the stent is provided with a coil, the adjusting handle is fixedly connected with the silk thread. The silk thread is sleeved with the coil through the hole. The controllable esophageal stent release pusher of this utility model can controllably and accurately release the esophageal stent to the narrow part of the esophagus, and the stent can be released and recovered freely, which significantly improves the success rate and accuracy of esophageal stent release and reduces the occurrence of complications.

However, all of the above stent conveyors need to place the stent in the stent cavity in advance. Once placed, the stent will not be easily removed and cannot be used immediately as soon as it is placed. In this way, the stent will always be placed in the stent conveyor if long-distance transportation or long-term waiting is required. The long-term placement will affect the expansion force of the stent, which is not easy to quickly restore the natural tension, thereby affecting the effect of surgery.

SUMMARY OF THE INVENTION

The invention discloses a stent delivery system, comprising:

an outer sleeve assembly, including an outer sleeve body, an outer sleeve handle fixed to the rear end of the outer sleeve body, and an outer sleeve tip connected to the front end of the outer sleeve body, the outer sleeve handle is provided with an axial through-hole having the same diameter as the inner diameter of the outer sleeve body, and the outer diameter of the outer sleeve tip decreases stepwise from front to back;

an inner sleeve assembly, including a push tube sleeved in the outer sleeve body, an inner sleeve handle fixed to the rear end of the push tube, a stent placing tube connected to the front end of the push tube, and an inner sleeve tip set at the front end of the stent placing tube, the outer diameter of the push tube is adapted to the inner diameter of the outer sleeve body to provide an axial pushing force, the outer diameter of the push tube is greater than the outer diameter of the stent placing tube, the inner sleeve tip is provided with an axial through-hole having the same diameter as the inner diameter of the stent placing tube, and the outer diameter of the rear end of the inner sleeve tip is fitted with the outer diameter of the front end of the outer sleeve tip, and the outer diameter of the inner sleeve tip gradually decreases from the rear end to the front end;

a snap ring, which is fixed on the outer wall of the push tube between the outer sleeve handle and the inner sleeve handle.

Preferably, the outer sleeve body includes a front stent covering tube and a rear outer sleeve covering tube, and the length of the stent covering tube is not less than the length of the stent placing tube in the inner sleeve assembly, the stent covering tube is used to sleeve on the outside of the stent placing tube to cover the built-in stent.

Further, the inner diameter of the stent covering tube is greater than the inner diameter of the outer sleeve covering the tube.

Preferably, the outer sleeve handle includes a grip portion and an anti-slip portion, the grip portion and the anti-slip portion are detachably connected as a whole, and the connection method thereof is screwing or snapping, or the grip portion and the anti-slip portion are integrally formed.

Further, the anti-slip portion is provided with a plurality of protrusions along its outer periphery, and the protrusions are linear or curved, or the outer surface of the anti-slip portion is provided with multiple bumps.

Preferably, the front end and the rear end of the outer sleeve handle are hemispherical.

Further, the stent placing tube and the push tube of the inner sleeve assembly is connected by a connecting member, which includes a small-diameter portion for inserting the stent placing tube, a large-diameter portion for inserting the push tube, and a push table located therebetween, the push table is provided with a through-hole, and the inner diameter of the through-hole is smaller than the inner diameter of the small-diameter portion and the large-diameter portion.

Preferably, the inner sleeve handle includes a spherical portion and a handle portion, the rear end of the spherical portion is hemispherical, the outer diameter of the handle portion gradually decreases from back to front.

Further, an instrument channel and a water inlet channel are provided inside the push tube and the stent placing tube, the push tube part of the outer sleeve handle, and the inner sleeve handle is provided with a water inlet nipple.

Preferably, the outer periphery of the front end of the push tube is equipped with a developing ring.

In summary, the stent delivery system, according to the present invention, is provided with an outer sleeve tip at the front end of the outer sleeve body. The outer diameter of the outer sleeve tip decreases stepwise from back to front, which makes the outer sleeve tip is convenient to cooperate with the stent accommodating tube of the stent auxiliary importing device. The head end portion of the stent accommodating tube is sleeved on the front end of the outer sleeve tip, which has a thinner outer diameter during use, the front surface of the head end of the stent accommodating tube abuts on the stepped surface of the outer sleeve tip, providing a thrust to the tube body portion of the outer sleeve tip which has a thicker outer diameter, so that the outer sleeve body moves backward in the axial direction, accompanying this, the exposed stent placing tube enters the stent accommodating tube, and the stent already placed in the stent accommodating tube can be transferred from the stent accommodating tube to the stent placing tube, there is no need to place the stent on the stent conveyor for a long time in advance, it can be used immediately as soon as it is placed, and it is very convenient to use. In addition, the outer diameter of the push tube of the present invention is greater than the outer diameter of the stent placing tube, which can reduce the gap between the push tube and the outer sleeve body and increase the pushing force of the push tube, the practical value is very high.

In order to make the above content of the present invention more comprehensible, preferred embodiments are hereinafter described in detail in conjunction with the accompanying drawings.

BRIEF DESCRIPTION OF THE DRAWINGS

The present invention will be described below in conjunction with the accompanying drawings.

DETAILED DESCRIPTION OF THE INVENTION

The embodiments of the present invention are described in the following specific embodiments, and those skilled in the art can easily understand other advantages and effects of the present invention by the contents disclosed in the present specification.

Exemplary embodiments of the present invention will now be described with reference to the accompanying drawings. The present invention can be implemented in many different forms and is not limited to the embodiments described herein. These embodiments are provided for the purpose of exhaustively and completely disclosing the present invention, and to fully convey the scope of the present invention to those skilled in the art. The terms used in the exemplary embodiments shown in the drawings are not intended to limit the invention. In the accompanying drawings, the same units/elements are given the same reference numerals.

Unless otherwise stated, the terms (including technical and scientific terms) used herein have the ordinary meaning to those skilled in the art. In addition, it is also understandable that terms defined in commonly used dictionaries should be understood as having a meaning consistent with the context of the relevant art, which should not be construed as an idealized or overly formal meaning.

The First Embodiment

Figure 1:
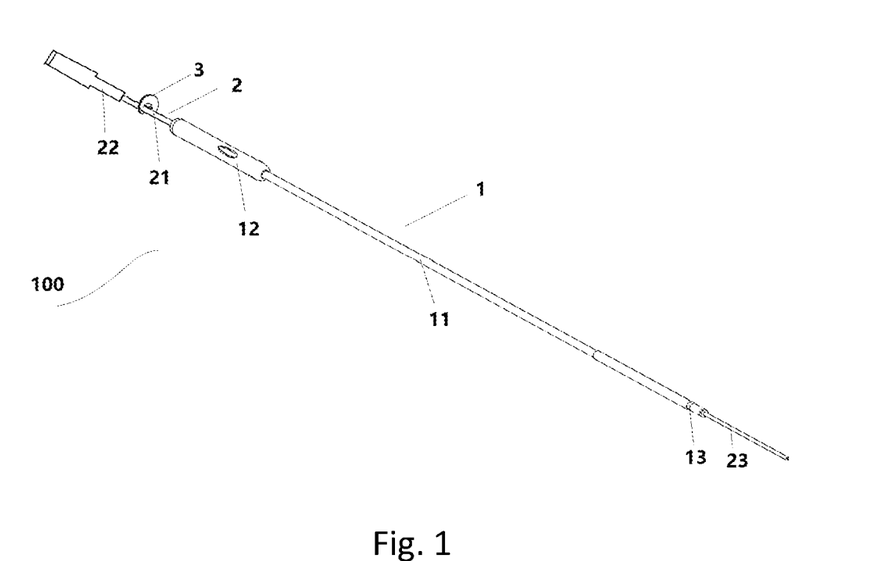
FIG. 1 is one kind of schematic diagram of the overall structure of a stent delivery system disclosed in each embodiment of the present invention.

As shown in FIG. 1, the first embodiment of the present invention discloses a stent delivery system 100, including an outer sleeve assembly 1, an inner sleeve assembly 2, and a snap ring 3. The outer sleeve assembly 1 includes an outer sleeve body 11; an outer sleeve handle 12 fixed to the rear end of the outer sleeve body 11, and an outer sleeve tip 13 connected to the front end of the outer sleeve body 11, in which the outer sleeve handle 12 is provided with an axial through-hole having the same diameter as the inner diameter of the outer sleeve body and the outer diameter of the outer sleeve tip 13 decreases stepwise from front to back. The inner sleeve assembly 2 includes a push tube 21 sleeved in the outer sleeve body 11, an inner sleeve handle 22 fixed to the rear end of the push tube 21, a stent placing tube 23 connected to the front end of the push tube 21, and an inner sleeve tip 24 (not shown in FIG. 1) set at the front end of the stent placing tube 23, in which the outer diameter of the push tube 21 is adapted to the inner diameter of the outer sleeve body 11 to provide an axial pushing force, the outer diameter of the push tube 21 is greater than the outer diameter of the stent placing tube 23, the inner sleeve tip 24 is provided with an axial through hole having the same diameter as the inner diameter of the stent placing tube 23, the outer diameter of the rear end of the inner sleeve tip 24 is fitted with the outer diameter of the front end of the outer sleeve tip 13, and the outer diameter of the inner sleeve tip 24 gradually decreases from the rear end to the front end. The snap ring 3 is fixed on the outer wall of the push tube 21 between the outer sleeve handle 12, and the inner sleeve handle 22.

Figure 2:
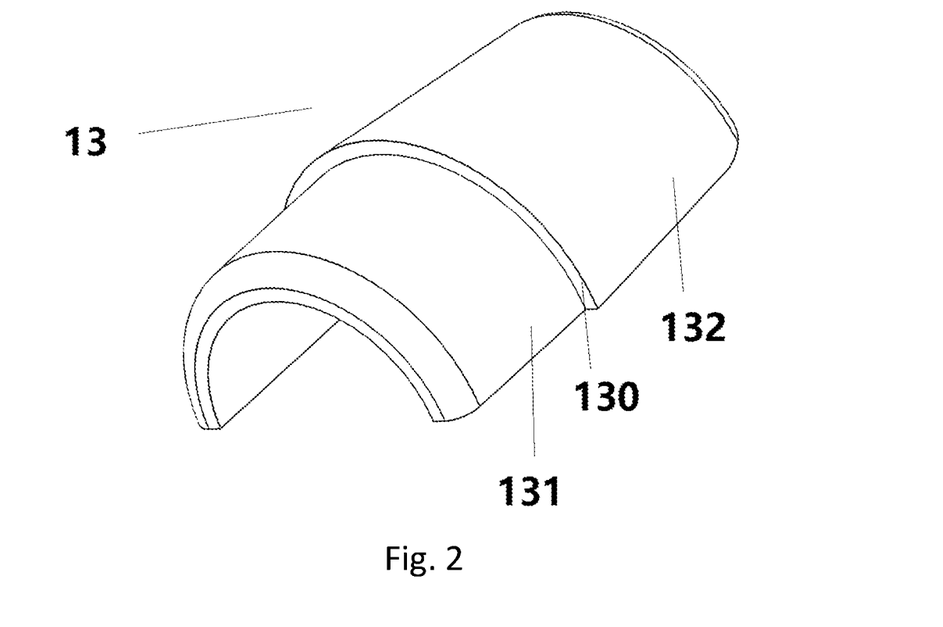
FIG. 2 is a cross-sectional view of an outer sleeve tip disclosed in each embodiment of the present invention.

In the first embodiment of the present invention, the outer diameter of the outer sleeve tip 13 decreases stepwise from back to front, which makes the outer sleeve tip 13 is convenient to cooperate with the stent accommodating tube of the stent auxiliary importing device. As shown in FIG. 2, the head end portion of the stent accommodating tube is sleeved on the front end 131 of the outer sleeve tip 13, which has a thinner outer diameter during use, and the front surface of the head end of the stent accommodating tube abuts on the stepped surface 130 of the outer sleeve tip 13, providing a thrust to the tube body portion 132 of the outer sleeve tip 13 which has a thicker outer diameter, so that the outer sleeve body 11 moves backward in the axial direction and the exposed stent placing tube 23 enters the stent accommodating tube, thereby the stent already placed in the stent accommodating tube can be transferred from the stent accommodating tube to the stent placing tube 23. Thus, there is no need to place the stent on the stent conveyor for a long time in advance, which can be used immediately as soon as it is placed, and is very convenient to use.

Specifically, the connection method of the outer sleeve tip 13 and the outer sleeve body 11 is bonding or screwing, or engaging connection by means of an interference fit, etc., and is not limited to the methods listed in this embodiment.

In this preferred embodiment, as shown in FIG. 1, the outer sleeve handle 12 may include a grip portion and an anti-slip portion, and the grip portion may be designed as a slightly concave arc-shaped cylinder in the middle, which is in line with the grip curve of a human hand and is convenient for the operator to hold the handle for operation. The anti-slip portion may be a non-slip structure provided along the outer periphery of the outer sleeve handle 12, and the non-slip structure may be a plurality of linear protrusions or various designs that can increase the coefficient of friction, such as multiple curved protrusions, multiple bumps, etc. Further, the grip portion and the anti-slip portion of the outer sleeve handle 12 of this embodiment may be detachably connected as a whole, such as connected as one by screwing, snapping, etc., or may be an integrally formed handle, which can be designed according to the actual needs and processing costs.

Furthermore, the front end and the rear end of the outer sleeve handle 12 are hemispherical. This design makes the transition curve among the various parts of the outer sleeve handle 12 smooth-going, which is convenient for griping without injuring the human hand and avoids damage to the human hand with high practical value.

In this preferred embodiment, the inner sleeve handle 22 may include a spherical portion at the rear end and a handle portion connected in front of the spherical portion. The rear end of the spherical portion is hemispherical, which is similar to the above-mentioned outer sleeve handle. The hemispherical design makes the transition curve among the various parts of the inner sleeve handle 22 smooth-going, which is convenient for griping without injuring the human hand and avoids damage to the human hand with high practical value. In addition, the outer diameter of the handle portion gradually decreases from back to front, which can increase the stress intensity between the inner sleeve handle and the push tube with a beautiful appearance.

Figure 4:
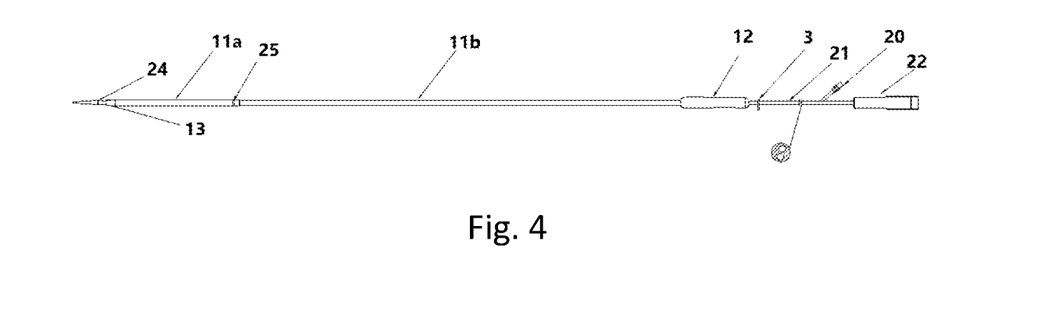
FIG. 4 is another kind of schematic diagram of the overall structure of another stent delivery system disclosed in each embodiment of the present invention.

Preferably, an axial instrument channel and a water inlet channel are provided inside the push tube 21 and the stent placing tube 23 communicating therewith. Accordingly, as shown in FIG. 4, a water inlet nipple 20 that communicates with the water inlet channel is provided on the outer wall of the push tube 21 between the outer sleeve handle 12, and the inner sleeve handles 22. The instrument channel can be used to insert a guidewire and the like into the patient's site. The water inlet nipple can be connected to an external pump to inject and pump water through the water inlet channel. The inner sleeve assembly 2 of this embodiment may also be provided with more axial channels for simultaneous insertion of two instruments for surgical operation or may be provided with separate independent water inlet channels and water outlet channels to inject and pump water separately.

More preferably, the outer periphery of the front end of the push tube 21 of this embodiment may be equipped with a developing ring 25. The developing ring 25 is displaced as the push tube 21 is pushed and pulled, and can be coordinated with X-rays to perform development positioning, thereby helping medical personnel to judge the moving position of the stent in the body lumen in real-time.

In the stent delivery system disclosed in this embodiment, the design of the outer sleeve tip 13 facilitates cooperation with the stent accommodating tube of the stent auxiliary importing device, which is no need to place the stent on the stent conveyor for a long time in advance, and is very convenient to use since it can be used immediately as soon as it is placed.

The Second Embodiment

As shown in FIG. 1, the second embodiment of the present invention discloses a stent delivery system 100, including an outer sleeve assembly 1, an inner sleeve assembly 2, and a snap ring 3. The outer sleeve assembly 1 includes an outer sleeve body 11; an outer sleeve handle 12 fixed to the rear end of the outer sleeve body 11, and an outer sleeve tip 13 connected to the front end of the outer sleeve body 11, in which the outer sleeve handle 12 is provided with an axial through-hole having the same diameter as the inner diameter of the outer sleeve body, and the outer diameter of the outer sleeve tip 13 decreases stepwise from front to back. The inner sleeve assembly 2 includes a push tube 21 sleeved in the outer sleeve body 11, an inner sleeve handle 22 fixed to the rear end of the push tube 21, a stent placing tube 23 connected to the front end of the push tube 21, and an inner sleeve tip 24 set at the front end of the stent placing tube 23, in which the outer diameter of the push tube 21 is adapted to the inner diameter of the outer sleeve body 11 to provide an axial pushing force, the outer diameter of the push tube 21 is greater than the outer diameter of the stent placing tube 23, the inner sleeve tip 24 is provided with an axial through-hole having the same diameter as the inner diameter of the stent placing tube 23, and the outer diameter of the rear end of the inner sleeve tip 24 is fitted with the outer diameter of the front end of the outer sleeve tip 13, and the outer diameter of the inner sleeve tip 24 gradually decreases from the rear end to the front end. The snap ring 3 is fixed on the outer wall of the push tube 21 between the outer sleeve handle 12, and the inner sleeve handle 22.

Figure 3:
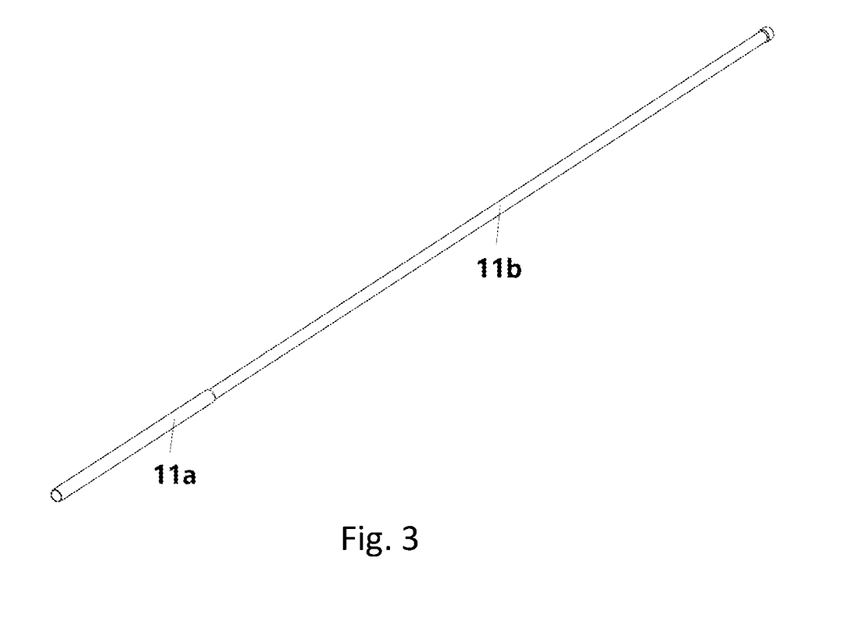
FIG. 3 is a schematic diagram of the overall structure of an outer sleeve body disclosed in the second embodiment of the present invention.

This embodiment is a modification of the first embodiment. In this embodiment, as shown in FIG. 3, the difference between this preferred embodiment and the first embodiment is that the inner diameter of the stent covering tube 11a is greater than the inner diameter of the outer sleeve covering tube 11b. The beneficial effects of this design are: on the one hand, the cavity space formed between the stent covering tube 11a and the stent placing tube 13 is sufficient, there is no need to over-compress when accommodating the self-expanding stent, which will damage the expansion force of the stent, on the other hand, the gap between the outer sleeve covering tube 11b and the push tube 21 becomes smaller, which is beneficial to increase the pushing force of the push tube 21, making the pushing and pulling of the tube body more convenient and labor-saving.

In this preferred embodiment, as shown in FIG. 1, the outer sleeve handle 12 may include a grip portion and an anti-slip portion, and the grip portion may be designed as a slightly concave arc-shaped cylinder in the middle, which is in line with the grip curve of a human hand and is convenient for the operator to hold the handle for operation. The anti-slip portion may be a non-slip structure provided along the outer periphery of the outer sleeve handle 12, and the non-slip structure may be a plurality of linear protrusions or various designs that can increase the coefficient of friction, such as multiple curved protrusions, multiple bumps, etc. Further, the grip portion and the anti-slip portion of the outer sleeve handle 12 of this embodiment may be detachably connected as a whole, such as connected as one by screwing, snapping, etc., or may be an integrally formed handle, which can be designed according to the actual needs and processing costs.

Furthermore, the front end and the rear end of the outer sleeve handle 12 are hemispherical. This design makes the transition curve among the various parts of the outer sleeve handle 12 smooth-going, which is convenient for griping without injuring the human hand, and avoids damage to the human hand with high practical value.

In this preferred embodiment, the inner sleeve handle 22 may include a spherical portion at the rear end and a handle portion connected in front of the spherical portion. The rear end of the spherical portion is hemispherical and is similar to the above-mentioned outer sleeve handle. The hemispherical design makes the transition curve among the various parts of the inner sleeve handle 22 smooth-going, which is convenient for griping without injuring the human hand and avoids damage to the human hand with high practical value. In addition, the outer diameter of the handle portion gradually decreases from back to front, which can increase the stress intensity between the inner sleeve handle and the push tube with a beautiful appearance.

Preferably, an axial instrument channel and a water inlet channel are provided inside the push tube 21 and the stent placing tube 23 communicating therewith. Accordingly, as shown in FIG. 4, a water inlet nipple 20 that communicates with the water inlet channel is provided on the outer wall of the push tube 21 between the outer sleeve handle 12, and the inner sleeve handle 22. The instrument channel can be used to insert a guidewire and the like into the patient's site. The water inlet nipple can be connected to an external pump to inject and pump water through the water inlet channel. The inner sleeve assembly 2 of this embodiment may also be provided with more axial channels for simultaneous insertion of two instruments for surgical operation or may be provided with separate independent water inlet channels and water outlet channels to inject and pump water separately.

More preferably, the outer periphery of the front end of the push tube 21 of this embodiment may be equipped with a developing ring 25. The developing ring 25 is displaced as the push tube 21 is pushed and pulled, and can be coordinated with X-rays to perform development positioning, thereby helping medical personnel to judge the moving position of the stent in the body lumen in real-time.

The Third Embodiment

As shown in FIG. 1, the third embodiment of the present invention discloses a stent delivery system 100, including an outer sleeve assembly 1, an inner sleeve assembly 2, and a snap ring 3. The outer sleeve assembly 1 includes an outer sleeve body 11, an outer sleeve handle 12 fixed to the rear end of the outer sleeve body, and an outer sleeve tip 13 connected to the front end of the outer sleeve body, in which the outer sleeve handle 12 is provided with an axial through-hole having the same diameter as the inner diameter of the outer sleeve body, and the outer diameter of the outer sleeve tip 13 decreases stepwise from front to back. The inner sleeve assembly 2 includes a push tube 21 sleeved in the outer sleeve body 11, an inner sleeve handle 22 fixed to the rear end of the push tube 21, a stent placing tube 23 connected to the front end of the push tube 21, and an inner sleeve tip 24 set at the front end of the stent placing tube 23, in which the outer diameter of the push tube 21 is adapted to the inner diameter of the outer sleeve body 11 to provide an axial pushing force, the outer diameter of the push tube 21 is greater than the outer diameter of the stent placing tube 23, the inner sleeve tip 24 is provided with an axial through hole having the same diameter as the inner diameter of the stent placing tube 23, the outer diameter of the rear end of the inner sleeve tip 24 is fitted with the outer diameter of the front end of the outer sleeve tip 13, and the outer diameter of the inner sleeve tip 24 gradually decreases from the rear end to the front end. The snap ring 3 is fixed on the outer wall of the push tube between the outer sleeve handle 12, and the inner sleeve handle 22.

Figure 5A:
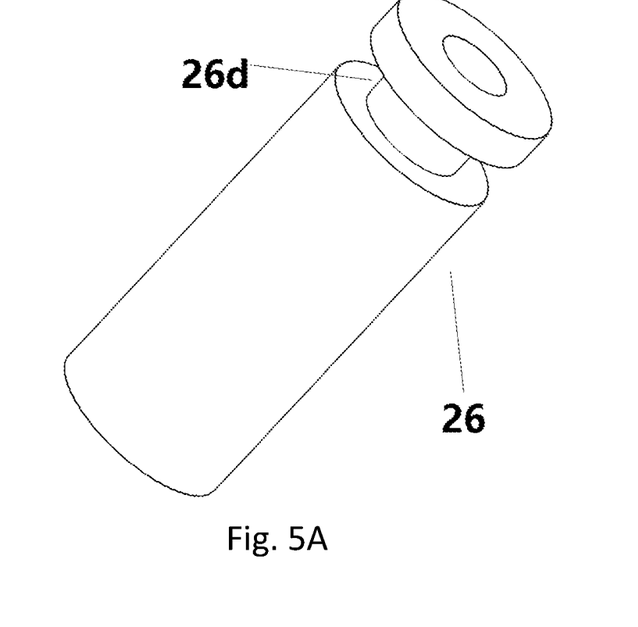
FIG. 5A is a schematic diagram of the overall structure of a connecting member disclosed in the third embodiment of the present invention.
Figure 5B:
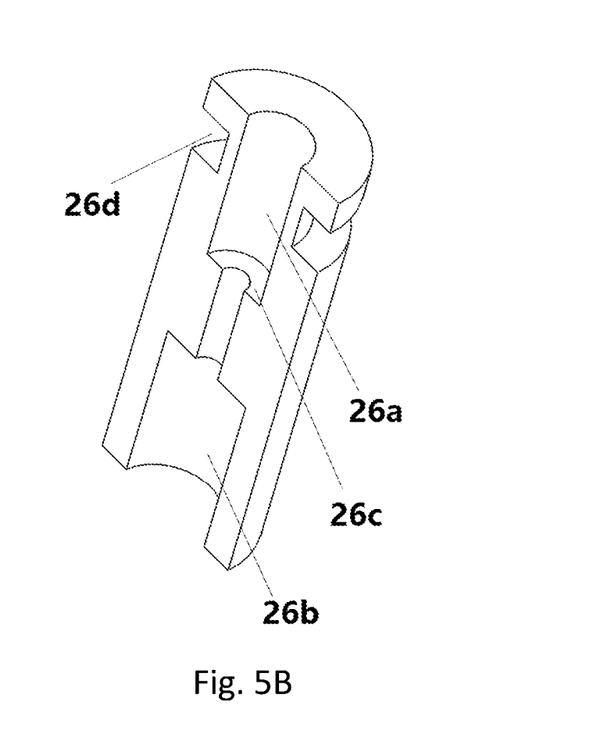
FIG. 5B is a cross-sectional view of the connecting member disclosed in the third embodiment of the present invention.

As shown in FIG. 1, FIG. 5-1, and FIG. 5-2, in this embodiment, this embodiment is different from the previous embodiment in that the stent placing tube 23 and the push tube 21 of the inner sleeve assembly 2 is connected by a connecting member 26, which includes a small-diameter portion 26a for inserting the stent placing tube, a large-diameter portion 26b for inserting the push tube, and a push table 26c located therebetween. The push table 26c is provided with a through-hole, which communicates the small-diameter portion 26a and the large-diameter portion 26b, and the inner diameter of the through-hole is smaller than the inner diameter of the small-diameter portion and the large-diameter portion. In use, the stent placing tube 23 is embedded in the small-diameter portion 26a and abuts on the front surface of the pushing table 26c, the push tube 21 is embedded in the large-diameter portion 26b and abutting on the rear surface of the pushing table 26c, and the through-hole of the pushing table 26c connects the lumen of the placing tube 23 and the push tube 21. Preferably, the inner diameters of the push tube 21, the through-hole of the pushing table 26c, and the stent placing tube 23 are equal, thereby forming a smooth-going transition lumen, which can constitute an instrument channel or a water inlet channel.

In this preferred embodiment, as shown in FIG. 1, the outer sleeve handle 12 may include a grip portion and an anti-slip portion, and the grip portion may be designed as a slightly concave arc-shaped cylinder in the middle, which is in line with the grip curve of a human hand and is convenient for the operator to hold the handle for operation. The anti-slip portion may be a non-slip structure provided along the outer periphery of the outer sleeve handle 12, and the non-slip structure may be a plurality of linear protrusions or various designs that can increase the coefficient of friction, such as multiple curved protrusions, multiple bumps, etc. Further, the grip portion and the anti-slip portion of the outer sleeve handle 12 of this embodiment may be detachably connected as a whole, such as connected as one by screwing, snapping, etc., or may be an integrally formed handle, which can be designed according to the actual needs and processing costs.

Furthermore, the front end and the rear end of the outer sleeve handle 12 are hemispherical. This design makes the transition curve among the various parts of the outer sleeve handle 12 smooth-going, which is convenient for griping without injuring the human hand and avoids damage to the human hand with high practical value.

In this preferred embodiment, the inner sleeve handle 22 may include a spherical portion at the rear end and a handle portion connected in front of the spherical portion, the rear end of the spherical portion is hemispherical and is similar to the above-mentioned outer sleeve handle. The hemispherical design makes the transition curve among the various parts of the inner sleeve handle 22 smooth-going, which is convenient for griping without injuring the human hand and avoids damage to the human hand with high practical value. In addition, the outer diameter of the handle portion gradually decreases from back to front, which can increase the stress intensity between the inner sleeve handle and the push tube with a beautiful appearance.

Preferably, an axial instrument channel and a water inlet channel are provided inside the push tube 21 and the stent placing tube 23 communicating therewith. Accordingly, as shown in FIG. 4, a water inlet nipple 20 that communicates with the water inlet channel is provided on the outer wall of the push tube 21 between the outer sleeve handle 12, and the inner sleeve handle 22. The instrument channel can be used to insert a guidewire and the like into the patient's site. The water inlet nipple can be connected to an external pump to inject and pump water through the water inlet channel. The inner sleeve assembly 2 of this embodiment may also be provided with more axial channels for simultaneous insertion of two instruments for surgical operation or may be provided with separate independent water inlet channels and water outlet channels to inject and pump water separately.

More preferably, the outer periphery of the front end of the push tube 21 of this embodiment may be equipped with a developing ring 25. The developing ring 25 is displaced as the push tube 21 is pushed and pulled, and can be coordinated with X-rays to perform development positioning, thereby helping medical personnel to judge the moving position of the stent in the body lumen in real-time.

Further, a concave ring 26d is provided on the outer peripheral wall of the connecting member 26, and the developing ring 25 can be embedded in the concave ring 26d, so that the position of the developing ring is fixed and does not fall off due to repeated push-pull friction between the outer sleeve body and the push tube of the inner sleeve assembly, reducing the risk of instrument damage.

The connecting member of this embodiment connects the push tube with a thicker outer diameter and the stent placing tube with a thinner outer diameter, which not only increases the stability of the connection, but also the inner wall of the inner cavity formed inside in the push tube and the stent placing tube is smoothly transitioned, and there is no step-ups and downs between each other so that the guidewire can smoothly advance along the inner cavity without obstruction, no bending deformation occurs, and the convenience of surgical operation is increased, and reduces the damage of instrument or human body.

In summary, the stent delivery system according to the present invention is provided with an outer sleeve tip at the front end of the outer sleeve body, and the outer diameter of the outer sleeve tip decreases stepwise from back to front, which makes the outer sleeve tip is convenient to cooperate with the stent accommodating tube of the stent auxiliary importing device. The head end portion of the stent accommodating tube is sleeved on the front end of the outer sleeve tip which has a thinner outer diameter during use, the front surface of the head end of the stent accommodating tube abuts on the stepped surface of the outer sleeve tip, providing a thrust to the tube body portion of the outer sleeve tip which has a thicker outer diameter, so that the outer sleeve body moves backward in the axial direction, accompanying this, the exposed stent placing tube enters the stent accommodating tube, and the stent already placed in the stent accommodating tube can be transferred from the stent accommodating tube to the stent placing tube, there is no need to place the stent on the stent conveyor for a long time in advance, it can be used immediately as soon as it is placed, and it is very convenient to use. In addition, the outer diameter of the push tube of the present invention is greater than the outer diameter of the stent placing tube, which can reduce the gap between the push tube and the outer sleeve body, and increase the pushing force of the push tube, the practical value is very high.

In addition, the above-mentioned embodiments of the present invention merely exemplarily illustrate the principle and effects of the present invention and are not intended to limit the present invention. Any person skilled in the art can modify or change the above embodiments without departing from the spirit and scope of the present invention. Therefore, all equivalent modifications or changes made by those skilled in the art without departing from the spirit and technical ideas disclosed by the present invention should still be covered by the claims of the present invention.

The invention claimed is:

1. A stent delivery system, comprising:
an outer sleeve assembly, including an outer sleeve body, an outer sleeve handle fixed to a rear end of the outer sleeve body, and an outer sleeve tip connected to a front end of the outer sleeve body, in which the outer sleeve handle is provided with an axial through hole having a same diameter as an inner diameter of the outer sleeve body,
an inner sleeve assembly, including a push tube sleeved in the outer sleeve body, an inner sleeve handle fixed to the rear end of the push tube, a stent placing tube connected to the front end of the push tube, and an inner sleeve tip set at the front end of the stent placing tube, in which the outer diameter of the push tube is adapted to the inner diameter of the outer sleeve body to provide an axial pushing force, the outer diameter of the push tube is greater than the outer diameter of the stent placing tube, the inner sleeve tip is provided with an axial through hole having the same diameter as the inner diameter of the stent placing tube, the outer diameter of the rear end of the inner sleeve tip is fitted with the outer diameter of a front end of the outer sleeve tip, and the outer diameter of the inner sleeve tip gradually decreases from the rear end to the front end, a snap ring, which is fixed on an outer wall of the push tube and is provided between the outer sleeve handle and the inner sleeve handle, and the outer diameter of the outer sleeve tip decreases stepwise from the back to the front, including the front end, which has a thinner outer diameter, a stepped surface, and a tube body portion, which has a thicker outer diameter, the stepped surface is used for abutting with a front surface of a head end of a stent accommodating tube, the stent placing tube and the push tube of the inner sleeve assembly is connected by a connecting member, which includes a small-diameter portion for inserting the stent placing tube, a large-diameter portion for inserting the push tube, and a push table located therebetween, the push table is provided with a through hole, and the inner diameter of the through hole is smaller than the inner diameter of the small-diameter portion and the large-diameter portion.

2. The stent delivery system according to claim 1, wherein the outer sleeve body includes a front stent covering tube and a rear outer sleeve covering tube, and a length of the stent covering tube is not less than a length of the stent placing tube in the inner sleeve assembly, and the stent covering tube is used to sleeve on an outside of the stent placing tube to cover a built-in stent.

3. The stent delivery system according to claim 2, wherein the inner diameter of the stent covering tube is greater than the inner diameter of the outer sleeve covering tube.

4. The stent delivery system according to claim 1, wherein the front end and the rear end of the outer sleeve handle are hemispherical.

5. The stent delivery system according to claim 1, wherein the inner sleeve handle includes a spherical portion and a handle portion, the rear end of the spherical portion is hemispherical, the outer diameter of the handle portion gradually decreases from back to front.

6. The stent delivery system according to claim 1, wherein an outer periphery of the front end of the push tube is equipped with a developing ring.

* * * * *